US011197642B2

(12) United States Patent
Freeseman-Freeman et al.

(10) Patent No.: US 11,197,642 B2
(45) Date of Patent: Dec. 14, 2021

(54) SYSTEMS AND METHODS OF ADVANCED WARNING FOR CLINICAL DETERIORATION IN PATIENTS

(71) Applicant: CERNER INNOVATION, INC., Kansas City, KS (US)

(72) Inventors: Laura Freeseman-Freeman, Kansas City, MO (US); Kathy N. Henson, Lee's Summit, MO (US); Thomas L. Higgins, Longmeadow, MA (US); Maureen Stark, Bel Air, MD (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

(21) Appl. No.: 16/731,747

(22) Filed: Dec. 31, 2019

(65) Prior Publication Data
US 2020/0214648 A1 Jul. 9, 2020

Related U.S. Application Data

(60) Provisional application No. 62/786,662, filed on Dec. 31, 2018.

(51) Int. Cl.
*A61B 5/00* (2006.01)
*G16H 50/20* (2018.01)
*G16H 50/30* (2018.01)
*G16H 80/00* (2018.01)
(Continued)

(52) U.S. Cl.
CPC ............ *A61B 5/747* (2013.01); *A61B 5/7264* (2013.01); *A61B 5/7275* (2013.01);
(Continued)

(58) Field of Classification Search
CPC ..... A61B 5/747; A61B 5/7282; A61B 5/7275; A61B 5/7264; A61B 2505/03;
(Continued)

(56) References Cited

U.S. PATENT DOCUMENTS 8,100,829 B2 * 1/2012 Rothman ............... G16H 50/70
600/300
8,595,159 B2 * 11/2013 McNair .................. A61B 5/024
706/12

(Continued)

*Primary Examiner* — Eric Blount
(74) *Attorney, Agent, or Firm* — Shook, Hardy & Bacon LLP

(57) ABSTRACT

Methods and systems determine risks of deterioration of hospitalized or other monitored or cared-for patients, for example in a treatment facility such as a hospital or under home-health care. In embodiments, a warning or other instruction is issued to medical professionals to alert them that certain patients have moderate or high risk of transfer to a higher level of care or should be monitored more frequently. A medical professional can accept alerts regarding prediction of deterioration, causing a prophylactic transfer or increased monitoring, or a transfer or monitoring order can occur automatically. Data relating to all patients in a unit of a medical facility can be viewed including warnings relating to risk of transfer or deterioration, so that a medical facility can intervene prior to an event such as a cardiac event and/or plan to accommodate patients at higher levels of care or monitoring.

20 Claims, 7 Drawing Sheets

(51) Int. Cl.
*G16H 40/63* (2018.01)
*G16H 40/67* (2018.01)
*G16H 40/20* (2018.01)
*G16H 10/60* (2018.01)

(52) U.S. Cl.
CPC .......... *A61B 5/7282* (2013.01); *G16H 10/60* (2018.01); *G16H 40/20* (2018.01); *G16H 40/63* (2018.01); *G16H 40/67* (2018.01); *G16H 50/20* (2018.01); *G16H 50/30* (2018.01); *G16H 80/00* (2018.01); *A61B 2505/03* (2013.01)

(58) Field of Classification Search
CPC ........ G16H 50/20; G16H 50/30; G16H 80/00; G16H 40/63; G16H 40/67; G16H 40/20; G16H 10/60
USPC ...................................................... 340/573.1
See application file for complete search history.

(56) References Cited

U.S. PATENT DOCUMENTS

| | | | | |
|---|---|---|---|---|
| 9,113,778 | B2* | 8/2015 | McNair | G16H 40/20 |
| 9,532,721 | B2* | 1/2017 | Batchinsky | A61B 5/318 |
| 9,536,052 | B2* | 1/2017 | Amarasingham | G16H 50/30 |
| 10,950,350 | B2* | 3/2021 | Edmondson, III | G16H 50/30 |
| 2006/0206013 | A1* | 9/2006 | Rothman | G16H 10/60 600/300 |
| 2008/0214903 | A1* | 9/2008 | Orbach | G16H 10/65 600/301 |
| 2009/0093686 | A1* | 4/2009 | Hu | G16H 50/30 600/300 |
| 2012/0092156 | A1* | 4/2012 | Tran | A61B 5/369 340/539.12 |
| 2015/0213225 | A1* | 7/2015 | Amarasingham | G06F 19/00 705/2 |

* cited by examiner

| Patient List: ▼ | | List Maintenance | | | Patient Search: 🔍 | | | | |
|---|---|---|---|---|---|---|---|---|---|
| Patient | | Location | Diagnosis | Alerts | APACHE... | Mort... | Length of Stay | | P|A|R |
| Vas, Greg | 35 yrs | M 3S-309 | Bacterial Pneumonia | ⚠ CRITICAL | ↗ ↑51 | 26% | 5.0 | 5.8 | 1.2 |
| Johnson, Erin | 37 yrs | F 3S-310 | Coronary Artery Disease | ⚠ CRITICAL | ↗ ↑49 | 17% | 1.0 | 2.4 | 2.4 |
| Shumer, Cary | 59 yrs | M 3S-302 | Chest Pain | ⚠ HIGH | ↗ ↑42 | 26% | 3.5 | 4.5 | 1.0 |
| Carter, Joy | 65 yrs | F 3S-314 | Congestive Heart Failure | ⚠ MODERATE | ↘ 35 | 9% | 4.1 | 3.2 | 1.5 |
| Barr, Ronald | 72 yrs | M 3S-308 | Acute Myocardial Infarc... | NO ACTION | → 32 | 19% | 4.8 | 6.7 | 2.0 |
| Mertle, Wayne | 64 yrs | M 3S-307 | Subdural Hematoma | | → 30 | 10% | 4.1 | 4.9 | 0.8 |
| Gregts, Conner | 40 yrs | M 3S-301 | Upper GI Bleed | | → 29 | 8% | 2.1 | 4.1 | 2.1 |
| Rico, Carl | 64 yrs | M 3S-315 | Diabetic Ketoacidosis | | ↘ 24 | 2% | 3.8 | 2.2 | 1.4 |
| Smith, Tanya | 52 yrs | F 3S-304 | S/P Appendectomy | | ↘ 23 | 4% | 2.6 | 3.2 | 0.2 |
| Clemson, John | 29 yrs | M 3S-305 | Umbilical Hernia | | ↗ 22 | 4% | 3.1 | 7.0 | 4.3 |
| Doug, Carlos | 75 yrs | M 3S-313 | Right Hip Fracture | | ↗ 21 | 2% | 6.2 | 4.4 | 2.6 |
| Lamps, Regina | 35 yrs | F 3S-303 | Cellulitis Left Leg | | ↗ 19 | 1% | 2.5 | 3.3 | 0.5 |
| Curt, Arnold | 57 yrs | M 3S-311 | S/P Carotid Endarterec... | | → 18 | 7% | 4.1 | 3.6 | 1.2 |
| Pitt, Ryan | 36 yrs | M 3S-312 | Peripheral Vascular Dia... | | → 16 | 3% | 3.9 | 3.0 | 2.2 |
| Louise, Bill | 45 yrs | M 3S-306 | Glioblastoma | | ↘ 15 | 1% | 4.2 | 5.1 | 0.8 |

FIG. 4

SYSTEMS AND METHODS OF ADVANCED WARNING FOR CLINICAL DETERIORATION IN PATIENTS

This Non-Provisional Patent Application claims the benefit of U.S. Patent App. No. 62/786,662, filed Dec. 31, 2018, entitled "Systems and Methods of Advanced Warning for Clinical Deterioration in Patients," which is hereby incorporated by reference in its entirety.

BACKGROUND

Typical methods for monitoring patients for deterioration are based on manual observations by medical practitioners. For example, patients on a hospital floor or in a step-down unit may be monitored by nurses or other professionals at certain intervals for changes in their conditions in order to determine if a rapid response team or transfer to an intensive care unit is necessary. In many cases, various professionals each monitor a patient at different times while also monitoring other patients, and changes or trends in a patient's condition can be too subtle to perceive, and therefore only substantial changes in a patient's condition may be observed.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-storage media for warning medical professionals that a patient's condition is deteriorating and transfer to an intensive care unit (ICU) or other escalation may be more likely or necessary, including prophylactic transfer in some cases. In some cases, deterioration in adult inpatients is defined by a hard endpoint of transfer to a higher level of inpatient care, for example within the next 24 hours of patient care. By monitoring electronic medical records (EMRs) for subtle changes that would not be detected by one or more medical professionals treating many patients over time, embodiments of the invention can warn professionals that a patient's condition is deteriorating and the patient's care is likely to be upgraded. EMRs provide an amount of data that can be monitored at a subtle level over time despite more than one medical professional being involved with a patient's care. Data from EMRs including, for example, information received continuously or nearly-continuously from one or systems or devices monitoring a patient, or increases in interventions by medical professionals, can be nuanced and change too slowly for medical professionals to notice trends over time, but one or more trends can be used by embodiments of the present invention to predict whether a patient is at a moderate, high, or critical risk for transfer to a higher level of care. EMR data permits automated capture of severity-of-illness data including acute physiologic changes that are useful for automated early warning systems, and, in embodiments of the present invention, integration and use of the now-abundant EMR data can be achieved.

This level of data may not have been available prior to EMRs, and/or medical professionals with multiple patients may not be able to detect small changes in one patient during the intervals where data is collected about a patient. In some cases, a prediction of deterioration may lead to a patient being transferred to an ICU or step-down treatment, or another elevated level of care with additional monitoring, for example. In embodiments, additional monitoring is used to continue predicting deterioration, in some cases at smaller intervals (such as two-hour intervals) because the data is available after increased monitoring. In some cases, transfer can be from a medical-surgical ward to an intensive care or progressive/intermediate care unit.

Embodiments of the present invention include warnings or alerts to medical professionals based on models of data, including in some cases data from distributed data sources. A patient's data can be analyzed at a 24-hour mark, when four sets of data for the patient are available based on 8-hour intervals or time points during the 24-hour period. The four sets of data can be used to determine four scores relating to the patient's severity of illness, and to determine, for example, three changes or trends associated with the scores over time. Certain sequences or patterns of changes or trends (for example, the four sequences represented by "uff," "ufu," "uuf," and "uuu") of the twenty-seven combinations of possible sequences of three (using Up, Down, and Flat) are used to determine whether to display a particular deterioration warning for a patient, such as a critical level of deterioration risk, and can be continuously updated over time.

In this example, using sequences of three vectors or representations of changes of SOI scores for a patient, twenty-seven possible combinations of Up, Down, and Flat exist (in some cases accounting for or using only significant indications of Up, Down, and Flat, such as applying a margin of error, and in some cases accounting for missing or null data points). Of these twenty-seven combinations for this particular illustration of a sequence of vectors (which can include more in some cases, such as sequences of five or ten, in some cases where a system determines them to be valuable or significant), there are four combinations in this example with a relatively higher or substantially more significant risk of deterioration, for example in certain time period. In some cases these sequences alone are implanted to make predictions regarding patients. For various circumstances, certain numbers of combinations of vectors or changes in SOI scores can be identified as associated with a higher or substantially higher risk of deterioration or transfer, such as indicating an over 50% or 80% likelihood of transfer to higher care within the next 24 hours.

In some cases, the scores relating to a patient's severity of illness over three or more time intervals are used in combination with one or more equations to determine a level or risk of deterioration. For example, a series of logistic regression models can be used to investigate the role of individual elements in the identification of patients' risks of deterioration. For example, a multivariate logistic regression procedure can be used to adjust or refine determinations of deterioration alerts based on sequences of changes in scores, or certain sequences of changes in scores alone (such as sets of three) can be used. In embodiments, each calculation considers a patient's previous 24 hours of data, for example (or another time period, including changes over any time period during a patient's stay, for example from admission to a current point in time). The warnings can enable medical professionals to increase the monitoring of a patient and, in some cases, allow caregivers to prevent transfers of patients to higher levels of care. For example, an early, predictive warning could allow a nurse or physician to increase the intervals where a patient's vital signs or other data will be collected in order to detect subtle or early changes in vital signs or resulting scores relating to the severity of illness over intervals and resulting trends. In other cases, medical professionals could receive early warnings of patients that will likely need transfer in order to prepare accommodations for the patients. In embodiments, computer-based predictions for patient deterioration and/or transfer are improved, which can help avoid escalations or transfers of patients. In some cases, use of rapid response teams can be decreased by detecting deterioration of a patient sooner, based on data that medical professionals would not observe in the course of treatment.

BRIEF DESCRIPTION OF THE DRAWINGS

Embodiments are described in detail below with reference to the attached drawing figures, wherein:

FIG. 4 is an exemplary interface including a table of patients in a care predictor unit showing deterioration alerts, for example in one unit of a medical facility;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, the descriptions or terms herein should not be interpreted as implying any particular order among or between various steps disclosed unless and except when the order of individual steps is explicitly described.

Embodiments of the present invention are directed to methods, systems, and computer-storage media for providing early, proactive warnings to medical professionals that one or more patients' conditions are deteriorating. In some cases, the warning or alert enables medical professionals to prevent a transfer to a higher level of care, such as an ICU. In some cases, a warning allows a medical professional to begin monitoring a patient at more frequent intervals, or to prepare a facility for an upgrade in care for a certain patient.

The present invention, including specific and non-conventional techniques and combinations of techniques that improve systems relating to electronic medical data or monitoring or storage devices, might be operational with numerous computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention can be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

Figure 1:
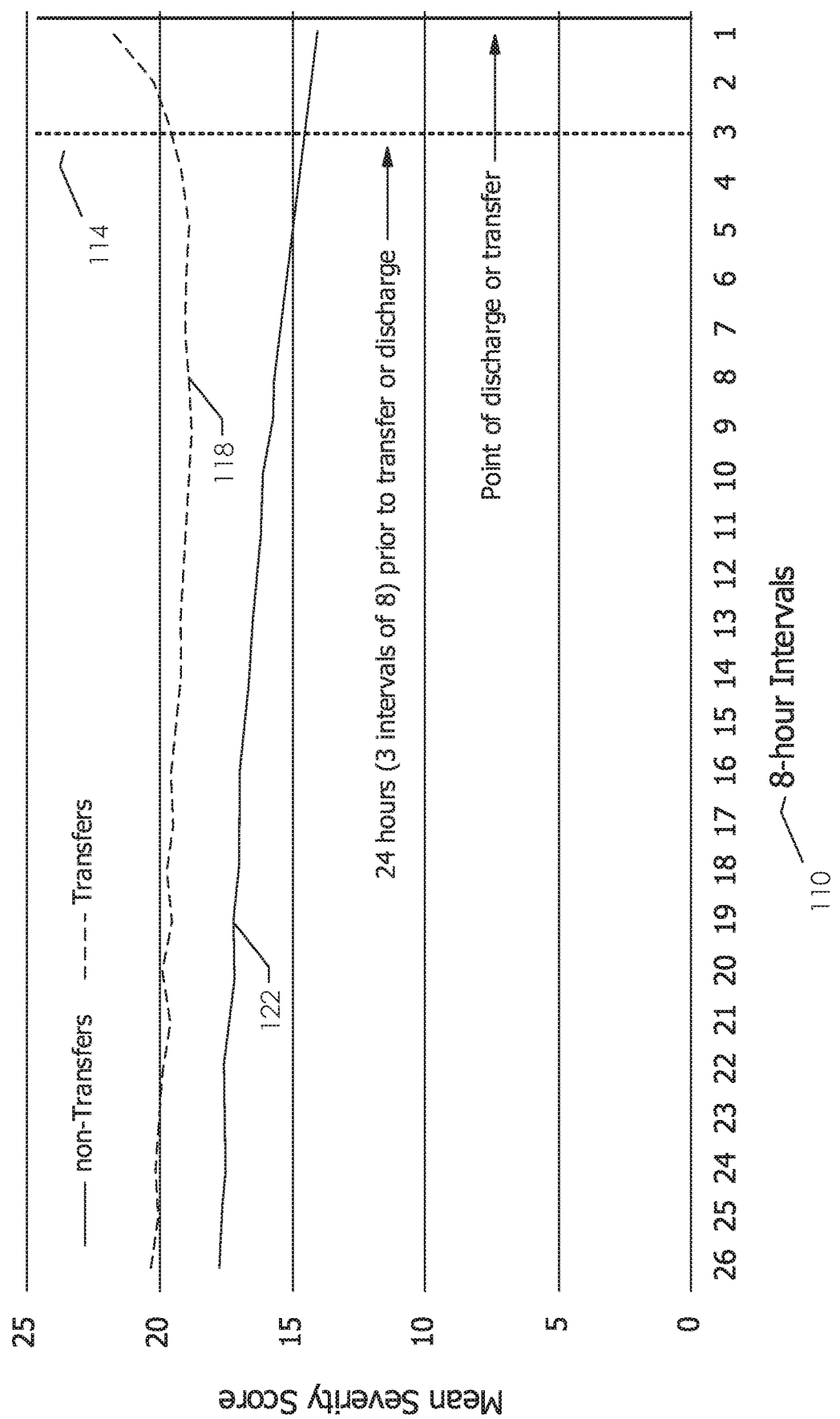
FIG. 1 is a chart illustrating relationships between eight-hour intervals of patient care and average severity scores considered in accordance with an embodiment of the present invention.

With reference to FIG. 1, the illustrative chart 100 shows intervals 110, such as the eight-hour intervals 110 in FIG. 1, numbered back from the end of patient's stay along the x-axis. For example, a patient may be discharged or transferred to another level of care at zero hours, on the far-right of the x-axis as shown in FIG. 1. The vertical line 114 indicated at marker "3" indicates the point 24 hours prior to transfer or discharge of a patient, which represents three eight-hour intervals prior to transfer or discharge. The dashed line 118 in chart 100 indicates patients who were eventually transferred, for example, while the solid line 122 indicates patients who were not transferred during care at a facility. In this example, chart 100 shows changes in average severity scores prior to transfer or discharge, including changes during the last three eight-hour intervals prior to transfer or discharge.

In some cases, one or more mean severity scores are severity of illness (SOI) scores for patients, which can correlate to mortality and length of stay for a patient, for example. SOI scores can be an overall SOI score as well as its major components: a Physiology Index, Comorbidity Index, and a Support Index, in one example, as discussed below, and can be a measure of a patient's current physiologic and therapeutic status. In some cases, an SOI score is determined based on a patient's initial 24 hours of hospitalization and can depend on multiple components, including inputs such as temperature, mean arterial pressure, resting heart rate, laboratory results, and/or a subset of comorbidities that are assigned points (such as, for example, bleeding, stroke, dementia, etc.). In some cases, diagnoses can have an additive or compounding effect with additional points or weight assigned for cases with more than one diagnoses or certain combinations of diagnoses.

In embodiments, the direction, magnitude, and velocity of changes in SOI scores throughout a patient's hospital stay are considered to create a new time series of SOI values for a patient. Different measures of trends in patients' SOI scores over a 24-hour period, for example scores calculated at a beginning time point and at three successive 8-hour intervals, can be considered, including the slope, range, moving averages, and root-mean square of successive differences (RMSSD), in embodiments, in some cases with a threshold of 20% or greater change to classify an SOI observation as "Up" or "Down," for example, as discussed in more detail below. Typically, vital signs that are ordered to be taken every eight hours can be used, but data from other intervals or the last valid value(s) can also be used. In embodiments, an analysis includes vital signs, laboratory values, individual comorbidities captured by ICD-10 coding, for example, and support items associated with a patient. Comorbidity can include bleeding/stroke, cancer, cardiac arrest or myocardial infraction, and/or valve disease, in some cases. It should be understood that various measures or time points within a period of duration can be used to calculate scores and trends as described, for example every two hours in an 8-hour period, or at the end of a 12-hour period where four instances of medical data relating to the patent (for example at the beginning and at 3-hour intervals) exist, or at every five or thirty minutes in a 2-hour period, with options that can be provided to users based on circumstances such as the availability of data, the length of a patient's stay, resources available, medical or public health considerations, etc. In some cases, systems can recommend time periods and/or data times and/or points for consideration based on the information available and the types of concerns at issue, such as evacuation concerns or patients dealing with additional time sensitivities such as pregnancy or impending surgery. Systems can predict or detect time points associated with patient data likely to have, or recognized as having, a higher certainty or usefulness to users.

In embodiments of the present invention, SOI scores and other data can be used to prevent a "failure to rescue" by medical professionals, for example by detecting clinical deterioration of a patient earlier, in some cases based on changes in data that are not noticeable by a team of medical professionals treating a patient. In some cases, a forewarning can provide additional time to alter a patient's path of decline, which could potentially avoid intervention by a rapid response team or avoid a "code blue," such as cardiac or respiratory arrest. Embodiments include an ongoing deterioration detection system that continuously assesses patients' electronic medical data and uses predictive analytics to measure a patient's risk for decline and provide a warning or notification to medical professionals. In some cases, equations are used, in addition to a sequence of three changes in SOI scores over a 24-four period, for example based on machine learning techniques or regression models, but in other cases certain sequence(s) of changes (e.g., "uff," "ufu," "uuf," and "uuu") can be used to identify a level of deterioration risk (e.g., a critical level) without additional calculations. In embodiments, each score calculated is associated with a patient's outcome and can be validated against data sets for accuracy, including against or while considering characteristics such as race, hospital bed size, and/or whether a hospital is a teaching hospital. For example, models for predicting dependent variables on the development data set can be used. In some cases, an overall model for predicting deterioration can include sub-models for physiology, support, and comorbidities using the same logistic regression approach or predictive analytics such as machine learning techniques.

On average, SOI scores decrease over time for patients consistent with their overall clinical improvement. But, the slope of the line can be steeper for patients who are discharged uneventfully than for those who deteriorate and go on to transfer to a higher level of care. For patients that begin to deteriorate, the rate of change in SOI scores can flatten then increase again prior to transfer, for example between 24 and 48 hours prior to transfer. Therefore, an SOI sequence associated with four data points or sets—for example taken at the beginning of a 24-hour time period and every eight hours or at three intervals (e.g., three eight-hour intervals)—can detect early signs of patients' need for an increased level of care before a critical event, such as a cardiac event. Embodiments of the present invention can consider and take advantage of data, such as certain patient measurements or other data points, and their change over time, as compared to analyses of static data such as measurements that are a snapshot from one point in time (or too few or too spread to provide a basis for determining a trend or pattern associated with a likelihood of deterioration). Embodiments can provide data over time such as changes in SOI scores, or rely on such data over time, and embodiments can use this information in conjunction with certain measurements or data in a static form, with the types of data optimized based on their usefulness in predictions or trends over time or their availability, and they can be weighted on these bases, as well.

In some cases, events can include expected complications of an underlying illness (for example cardiac arrhythmias after a myocardial infarction), but in other cases complications can be medical or surgical interventions (for example hospital-acquired infections or postoperative hemorrhage). In embodiments of the present invention, factors such as physiologic derangement (which can be quantified to be a certain degree), comorbidity, and/or clinical support variables are considered to predict the likelihood of deterioration of patients. Data for these factors can be determined from sequential clinical assessments, for example, that may be captured in electronic medical records, to detect subtle changes that a team of medical professionals could not observe as a trend during care of multiple patients. In embodiments, the difference between a more-recent SOI score and a previous SOI score is used to calculate each of the three values in one or more sequences (such as "Up"). In some cases, a percent change such as a threshold percent change between a later and an earlier SOI score is used to calculate values in one or more sequences (such as "Up"). In embodiments, a threshold amount of change may be zero percent, or a value set by a user or system, for example based on significance as detected by embodiments of a system, is used.

In embodiments, the SOI score is a combination of the Support Index (SI), the Physiology Index (PI), and the Comorbidity Index (CI), each multiplied by a scaling factor, representing the combined weighted values of the PI, SI, and CI. The score is independent of age, diagnosis, or location in the hospital; which can make the SOI useful as a comparative metric for evaluating patients across units, hospitals, or organizations. In embodiments, the indices are based on the previous 24 hours of EMR data, for example from a patient's hospital encounter, except for the Comorbidity Index. Capturing this variability can make the score less sensitive to any single data point. SOI scores range from 0-100, with higher values indicating increased severity. SOI scores can correlate with hospital mortality and length of stay, in some cases with a strong correlation. With respect to one embodiment, a categorization of comorbidities can be created and defined by groupings of ICD-10 codes, with Comorbidity Index ranges from 0 to 18, which includes in some cases seven items: coagulopathy/bleeding, cerebrovascular disease, heart failure, neuromuscular disease, dementia, chronic obstructive pulmonary disease (COPD), compromised immune system, and three interactions between terms (cerebrovascular with coagulopathy, cerebrovascular with COPD, and immune compromise with heart failure). A Comorbidity Index can provide an assessment of the prognostic burden imposed by chronic illness and can be a component within the SOI score, in embodiments.

Figure 2:
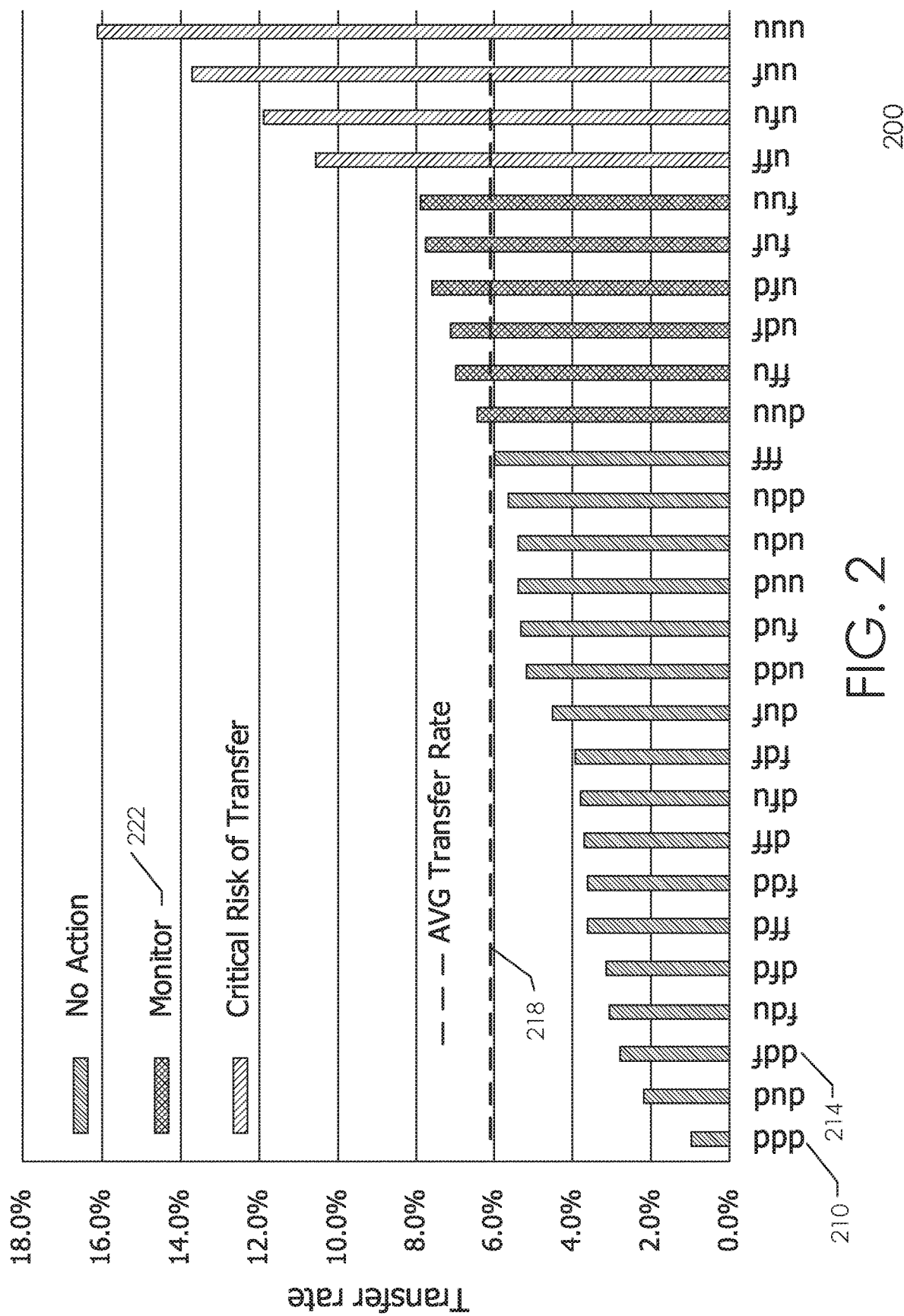
FIG. 2 is a chart illustrating sequences of results considered regarding deterioration of a patient in accordance with an embodiment of the present invention.

Turning to FIG. 2, a chart 200 of transfer rates versus patterns of SOI scores is shown. In chart 200, the x-axis shows patterns of changes in SOI scores, such as "Down-Down-Down" ("ddd"), or "Down-Down-Flat" ("ddf"). As one example, if three eight-hour intervals of SOI scores demonstrate a pattern of either "Up-Flat-Flat" ("uff" in FIG. 2), "Up-Flat-Up" ("ufu"), "Up-Up-Flat" ("uuf"), or "Up-Up-Up" ("uuu"), then a patient can be determined to be at a critical risk of deterioration or a critical risk of being transferred, for example to a higher level of care such as an ICU. In these cases, a medical professional could receive an alert that a patient is at critical risk of transfer, in order to intervene and attempt to prevent a transfer or an event such as a cardiac event. An exemplary risk associated with a "Down-Down-Down" pattern 210, and an exemplary risk associated with a "Down-Down-Flat" pattern 214, are illustrated in FIG. 2. The various exemplary risks shown in FIG. 2 are associated with different patterns and based on underlying data, and they can convey risks of transfer 210, 214 for each pattern, for example through a user interface of a mobile computing device in communication with systems and methods as described herein. The risks associated with the patterns can be displayed as compared to, or with overlaying data showing, one or more average transfer rate(s) 218, such as the overall average transfer rate or rates for certain conditions, demographic characteristic(s), or risk factors, for example. Options 222 for taking no action, monitoring, and/or flagging or directing that a high or critical risk of transfer be determined and graphically displayed exist in embodiments, as shown in FIG. 2. One or more sequences shown in FIG. 2 that are above a "Baseline" or zero risk level, but below a "critical" risk level (for example sequences shown to the left of "uff," "ufu," "uuf," and "uuu" on the x-axis) may be considered part of a "Monitor" category, and/or they may be considered to have a relative risk category of "low" or "moderate" risk (or higher that "low" or "moderate" but still lower than "critical").

In some cases, certain patterns can indicate that no action is necessary, such as "Flat-Down-Up" ("fdu"), while other patterns indicate a patient should be monitored or monitored more frequently, such as at two-hour intervals, for example. In the illustrative example in FIG. 2, the patterns "ddd" ("Down-Down-Down") through "fff" (Flat-Flat-Flat) are associated with relatively lower transfer rates and with a recommendation of "No Action" needed by medical professionals. Continuing with this example, the patterns "duu" ("Down-Up-Up") through "fuu" ("Flat-Up-Up") are associated with monitoring or increased monitoring, while the four patterns discussed above are associated with a high risk of transfer. In an example, the four patterns with the highest risk of transfer indicate patients that are 50% more likely to deteriorate to the point of requiring transfer to a higher level of care. Embodiments can use the relationship between these trends over time and the likelihood of deterioration to aid medical professionals and avoid failures to rescue. In one example, a threshold of at least a 20% change is used to determine if a patient's SOI score has increased or decreased during an eight-hour interval. Other intervals can be used, for example if a patient has not been in care for 24 hours or if more frequent electronic medical data is available to be analyzed. FIG. 2 illustrates twenty-seven exemplary, unique patterns of SOI scores during a sequence of three intervals, with the patterns ordered from left to right by their increased association with a risk of transfer.

As shown in the example in FIG. 2, three categories exist for the most-recent SOI score sequence associated with three intervals, such as three 8-hour intervals. For example, the sequences of three intervals labeled "No Action" (patterns "ddd" through "fff" on the x-axis) can be categorized as a "baseline" for patients with average or less than average risks of transfer. The next set of patterns on the x-axis ("duu" through "fuu") can be associated with an elevated risk of transfer and categorized as patients with a "moderate risk," or for some sequences or in some cases, as a "high risk." Finally, the last four patterns on the x-axis in this example ("uff" through "uuu") can be associated with patients categorized as "critical risk," which can indicate a significant risk of deterioration and/or transfer to a higher level of care such as an ICU. Patients categorized as "critical risk" can be subjects of interventions that may include fluid resuscitation, enhanced monitoring, or prophylactic transfer to the higher level of care. In some cases, a category of patients where the relative risk indicates to intervene, such as "critical risk," can have a risk of subsequent deterioration that is nearly 2.5 times that of patients in a "baseline" category. Users or providers of systems can configure risk categories, thresholds, labels, and display options, in some cases. For example, various patterns represented on the x-axis can be assigned to the category a "moderate" risk, while other sequences can be associated with a "high" or "critical" risk or other configured category, and these categories may be adjusted if certain calculations beyond sequences are implemented. A category or otherwise flagged set of patients may be shown graphically on a display, such as in color (e.g., color-coded text, such as shading, highlighting, or proximate indicators in a certain color, where the text can be additional and in color or otherwise existing text on an interface using a color) or with other additional images or text, for example text relating to an increased risk of transfer or text presenting an option for additional data to be captured for one or more patients.

Table 1, below, illustrates examples of pooled risks for various categories and the average transfer rates associated with each relative risk category. The values and Relative Risk Categories in Table 1 are exemplary illustrations. Other values indicating patients, transfers, and risk rates can be used to categorize patients in embodiments of the present invention. Patients can have a "Critical" Relative Risk Category with an even higher transfer rate and/or relative risk value than the "High Risk" category. In some cases, patients determined to have a Relative Risk above a value of 1.00 may be patients in a moderate-risk category (for example above 1.00 but still below a certain threshold of risk), while patients determined to be in "High" and/or "Critical" risk categories may be identified as above one or more thresholds of risk, for example relating to total patients and transfer rates or other calculations of relative risk.

| Relative Risk Category | Total Patients | Percent Patients | Transfers | Transfer Rate | Relative Risk |
|---|---|---|---|---|---|
| Baseline | 33,040 | 67.48% | 1,589 | 4.81% | 1.00 |
| Moderate Risk | 10,728 | 21.91% | 791 | 7.37% | 1.53 |
| High or Critical Risk | 5,193 | 10.61% | 587 | 11.30% | 2.35 |
| | 48,961 | 100.00% | 2,967 | 6.06% | |

In some cases, SOI scores over a series of three intervals can reveal a trend that accurately represents patients for the time period 24 to 48 hours prior to a transfer, which can be used to determine the likelihood of transfer for each patient in a facility as described above, for example. In some embodiments, SOI scores over a sequence of three intervals can be used in addition to or in combination with scores such as a Physiology Index (PI), Support Index (SI), or Comorbidity Index (CI), which can be absolute scores. These scores can be used in equations to predict outcomes such as mortality, length of stay, deterioration, and/or vent duration, for example, across different levels of care in medical facility, including an ICU. SOI scores over a sequence of three intervals can capture a patient's deterioration or add incremental value in conjunction with the use of the patient's absolute SI, PI, and CI scores or, in come cases, other physiological measures of trend.

A Physiology Index can capture a patient's physiologic variability in the prior 24 hours and can be comprised of four vital signs (heart rate, respiratory rate, temperature, and mean arterial pressure) and/or three laboratory values (hematocrit, platelet, and serum sodium), in embodiments. In one example, a Physiology Index is created with a two-step machine learning approach using, for instance, Genetic Algorithms and Particle Swarm Optimization. For laboratory values, only a minimum and maximum value are required over a 24-hour period, providing six lab components to the Physiology Index, in an embodiment of the present invention. In some cases, various treatments can impact a Physiology Index used to calculate an SOI score, such as antiarrhythmic treatment, non-invasive ventilation, intubation, dialysis, intravenous treatments, insulin, antibiotics, pacemaker placement, vasopressors, and/or inotropic treatments.

In embodiments, the four vitals and three laboratory values have been or can be individually tested to investigate the role of these individual measures over a patient's hospital stay, and, for example, a patient's respiratory rate can be a factor in a final model (patients with a higher "minimum" respiratory rate during their stay at a medical facility can be at less risk of transfer). In some cases, data relating to one or more indices such as the Physiology Index (including other indices and data discussed herein) can be based on data from 3-hour intervals or other time frames. The low, median, and high results for one or more vital sign measures can be used in the Physiology Index, in some cases. In embodiments, data such as physiology-related data may be received or considered on a more-or-less continuous basis, in near real-time and in some cases without any human intervention required to receive additional data, for example where one or more medical or monitoring devices are in communication with one or more components (or accessible by them) of embodiments of a system as described herein. In some cases data is intermittently received such as test results or specific, discrete monitoring or observations, such as meals or medications taken. Such information can be received or obtained by a system as soon as available or it can be requested or pushed to system based on parameters of configured settings.

One or more treatments can be used to remove points from a patient's Physiology Index score, as discussed, for example a pacemaker or antiarrhythmic treatment, because such treatments may be preventative or otherwise make certain escalations or effects less likely. Selected variables can be preprocessed to create new numeric features, categorical features, spline variables and individual flags. Variables can also be grouped into the three indices, for example. Variables can be evaluated using univariate (chi square, t-test) against the outcome of transfer to a higher level of care. Three of the four vital signs, heart rate (HR), respiratory rate (RR), and mean arterial pressure (MAP), are required to receive a physiology score and the subsequent SOI score in some cases. In the absence of a documented MAP, mean arterial pressure can be calculated using a formula MAP=⅓ systolic blood pressure+⅔ diastolic blood pressure, for example. In embodiments, the Support Index can comprise ten therapies identified by logistic regression from a list of more than forty potential therapies (pacemaker, artificial airway, invasive positive pressure ventilation (IPPV), non-invasive positive pressure ventilation (NIPPV), hemodialysis (HD), antiarrhythmic agents (IV or oral), intravenous antibiotics, inotropes (IV or oral), vasopressors (IV), and intravenous insulin). Fewer or more therapies may be used for the Support Index. The Support Index can be generated by attributing point values to any one or more of these ten therapies, for example, delivered during the last 24-hour period. In some cases, patients receive points associated with a Support Index if they receive therapy in the prior 24 hours. In embodiments, the trend of a Support Index over a patient's stay in a medical facility (for any time increments, for example over 24 hours) can be a key consideration in the model.

Figure 3:
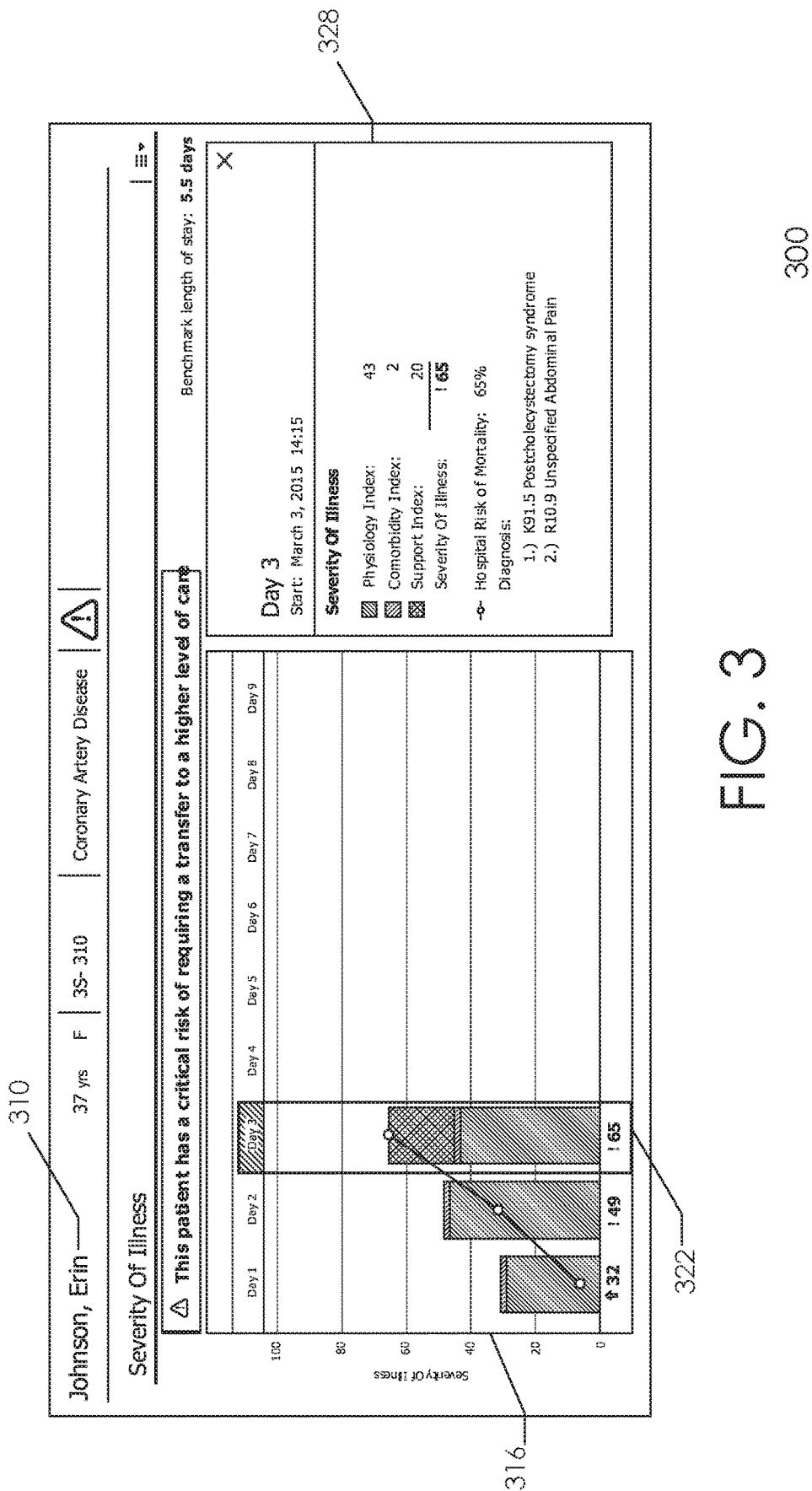
FIG. 3 is an exemplary view of data relating to a selected patient including a warning in accordance with an embodiment of the present invention.

FIG. 3 is an exemplary view 300 of a page, such as an MPage in an example, viewed by a medical professional. In the example in view 300, patient 310 has been selected for viewing, and view 300 includes the patient's age, gender, location in a medical facility, and diagnosis. In embodiments, view 300 includes a warning symbol such as text stating "Moderate," "High," or "Critical" risk, or an item such as a triangle icon including an exclamation point, which can alert a medical professional that at least one warning or alert is associated with patient 310. For example, a textual indicator can include a display of one or more warnings or risk categories such as the word "Moderate" or another first category can be in black text, the word "High" can be in orange text and bolded, or another second category (or similar terms or gradients in other languages, etc.) in a second color and/or style of text, and the term "Critical" can be in red font and/or bolded, etc., or another term or indicator of a highest level of deterioration risk. In this example, a warning exists that explains the selected patient 310 has a critical risk of requiring transfer to a higher level of care. The warning, in some cases, is based on the SOI scores in table 316 including the SOI of "65" shown for day 322 ("Day 3"). View 300 can also include panel 328 showing details of the SOI score for Day 3, such as a PI, CI, and SI, along with a Diagnosis and a value for a hospital risk of mortality. View 300 can also indicate a benchmark length of stay for patient 310. A medical professional can use the warning shown in view 300 to intervene with medical treatments, adjust the intervals of monitoring such as the frequency of when vital signs are recorded, or to prepare a medical facility and/or patient for transfer, for example. The SOI scores and the example of a warning in FIG. 3 based on a sequence of three changes in SOI scores, would not have been detected by multiple medical professionals because they depend on subtle changes analyzed over a sequence of EMRs.

Figure 5:
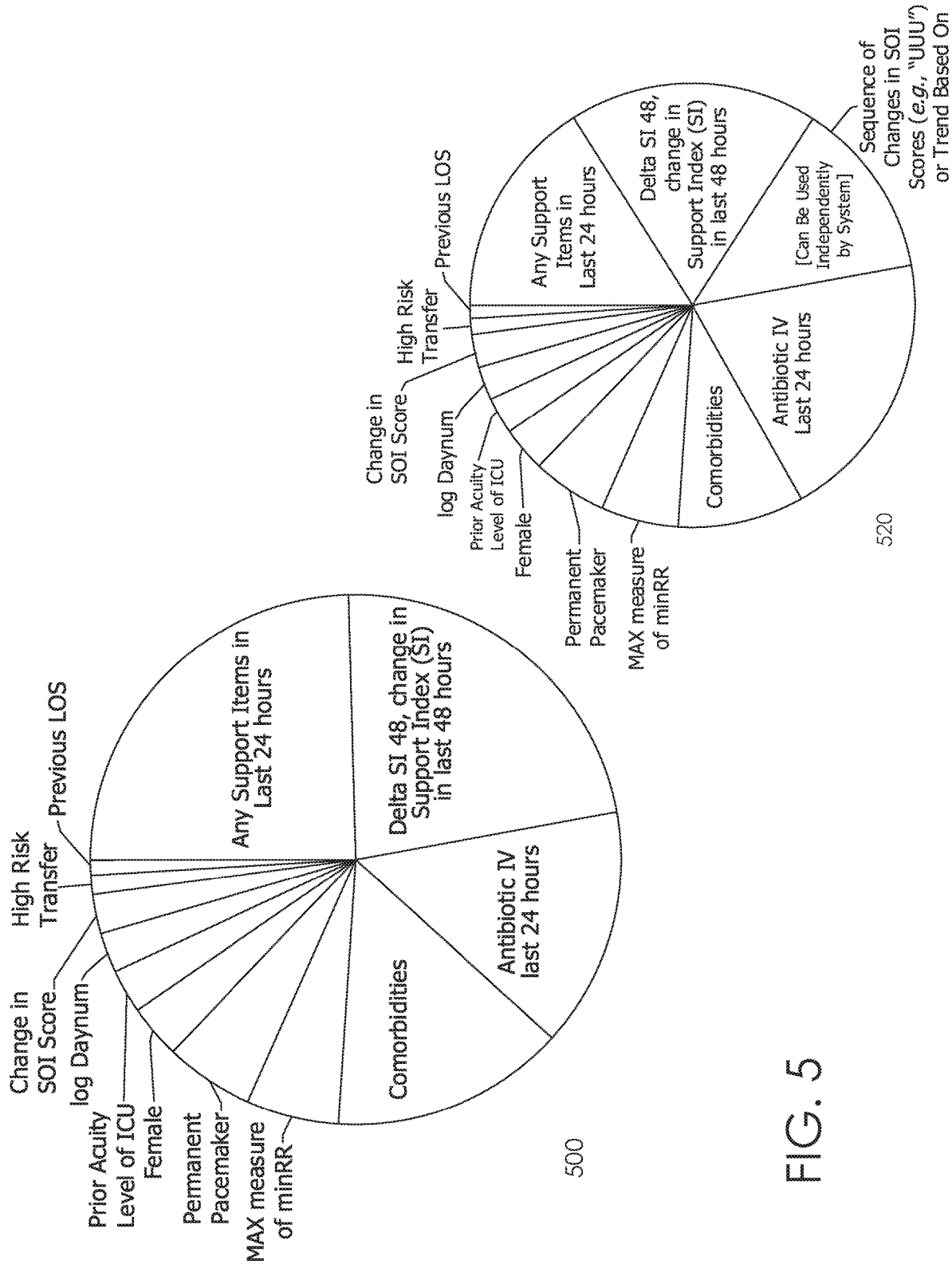
FIG. 5 is a chart illustrating examples of independent variables that can be considered regarding deterioration of a patient in accordance with an embodiment of the present invention.

FIG. 4 shows an illustrative interface 400 showing patients and other information, for example patient data that may be displayed for a critical care unit or facility via a dashboard or other display on a device, such as an overview of patients used by a medical professional, in accordance with an embodiment of the present invention. In this example, patients in a unit of a medical facility, or all patients in a medical facility, can be viewed using interface 400, so that medical professionals can view one or more warnings on a screen of a device, for example. In this embodiment, a Patient List "3S" is selected as shown by selection box 410, which has been set to "3S." A list of patients in patient column 418 shows the names or other identifiers of patients located in a medical unit labeled "3S," for example. Location column 424 can provide information regarding locations of patients within a medical unit "3S," in this example. Each patient's diagnosis or one or more historical or potential diagnoses for a patient can be listed in diagnosis column 430, and an alert column 436 can display an icon or other indication of an alert for each patient displayed using interface 400. In some cases, column 442 can include one or more indicators such as arrows or numbers, such as graphic indicators, statistics, or predictions, in some cases including one or more SOI values or trends associated with each patient. Mortality column 448 can indicate a percentage or other value associated with mortality. In some cases, patients can be displayed according to alerts, such as the alerts indicated in alert column 436, or according to the highest values in column 442 relating to patient outcomes, or according to mortality column 448 values. Continuing with the example in FIG. 4, length of stay column 454 shows each patient's length of stay (predicted length of stay and/or actual length of stay), in some cases including the length of stay on bed rest or in recovery, for example, or other types of stays in medical facilities, such as in acute care. In some cases column 454 shows or provides access to information relating to a Predicted stay, and Actual stay, and a Remaining length of stay for patients, as shown in one exemplary interface 400 at column 454. Interface 400 includes search box 460 that allows professionals to search for a particular patient, diagnosis, or other characteristic. The alerts indicated in FIG. 4 can be based on SOI scores as described herein, in some cases in combination with other absolute scores or other considerations. Various icons, symbols, or information can be included, for example in alert column 436, to enable an overview of patients in a unit and warnings or alerts associated with the patients. As shown in the illustrative interface 400 in FIG. 4, an exemplary patient 466 ("Vas, Greg") is shown with a diagnosis of Bacterial Pneumonia and one deterioration alert 478, as well as an SOI that has trended upwards since yesterday. Deterioration alert 478 can be determined according to a trend based on changes in severity of overall illness scores using four sets of data, for example, independent of any diagnoses. Patient 470 ("Shumer, Cary") is shown in FIG. 4 associated with alert 482, such as a graphical, color-coded or shaded, icon or symbol or textual note, flag, or warning. For example, as shown for patient 474 ("Carter, Joy"), the alert 486 for this patient is not as dark as alert 482, or it is in a different color (such as a dimmer or lighter color such as shade of gray). FIG. 5 includes first chart 500 of potential considerations such as examples of other independent variables that can contribute to determining a likelihood of deterioration of a patient including a likelihood that transfer may be needed or that additional monitoring should be employed, which can be implemented in all or in party along with one or more additional considerations (not shown) in varying degrees or weights (e.g., in ratios or according to different aspects than as specifically shown in the illustrative examples in FIG. 5). FIG. 5 also includes second chart 520 showing use of a combination of one of more (such as three consecutive) changes in SOI scores to determine a trend or a likelihood or other output independently (as stated in FIG. 5 at 520), or using such a sequence or pattern (or resulting trend) in combination with one or more other potential considerations, such as the illustrative examples in first chart 500 and included in second chart 520, in any amount of degrees or weight according to configurations or preferences, with the examples shown in FIG. 5 as optional or representational examples of considerations that can contribute to varying extents as shown for certain illustrations in FIG. 5. In some cases, the considerations in FIG. 5 are the remaining variables used to determine a deterioration score (in addition to an overall SOI score or sequence of scores, and/or SI, PI and/or CI scores). In embodiments of the present invention, ongoing validation and decay tracking can lead to updated coefficients and/or modifications in the specific independent variables considered. In the example in FIG. 5, embodiments of the present invention consider information that can be obtained from sequential clinical assessments, for example, any support items associated with a patient in the last 24 hour period, and any change in a patient's Support Index (SI) in the last 48 hours (last six eight-hour intervals), although these time periods can be adjusted. Embodiments can include changes in measurements over any time periods from admission to a current time period. Embodiments can also consider any intravenous antibiotics administered in the last 24 hours, for example. Other factors considered include comorbidities, MAX measure of minRR relating to respiration data or measurements, and/or a permanent pacemaker, for example. Additional factors could include gender, a prior acuity level of ICU, and/or a log Daynum relating to a number of days. Other considerations can be a change in SOI score, whether a patient has a high risk of transfer, and/or a previous length of stay (LOS) for a patient. In some cases, five other independent variables relate to a change in SOI scores, or a patient's need for support, which can together account for two-thirds of the remaining variability captured in one or more models. As discussed herein, one or more changes in SOI scores, such as a sequence of three changes based on data captured at four points in a 24-hour period, are used to determine risk in some cases without additional considerations, or such considerations could be embedded in or used to weight specific SOI score(s).

Figure 6:
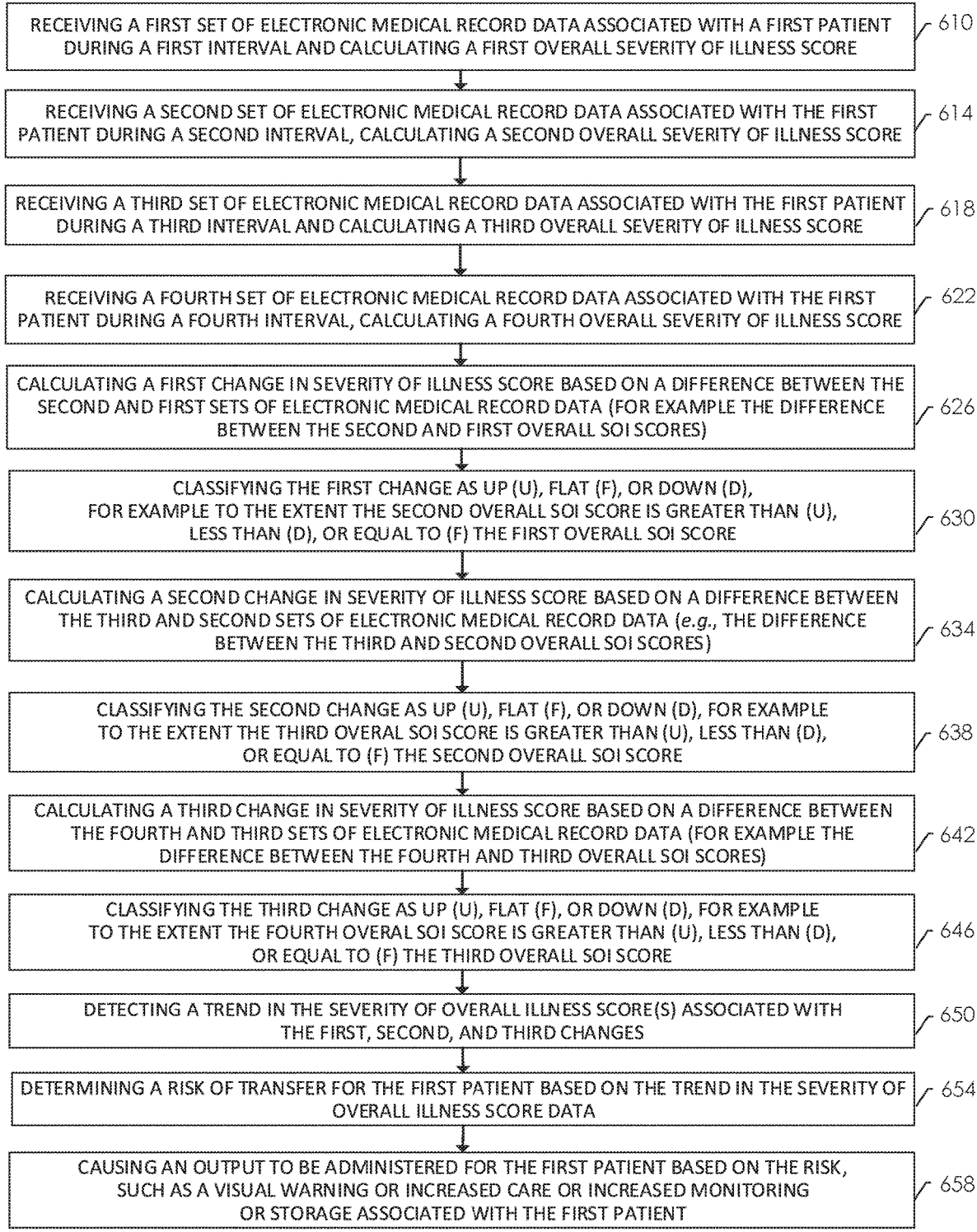
FIG. 6 is a diagram of aspects of systems in accordance with an embodiment of the present invention.

Turning to FIG. 6, a diagram 600 of one or more processes or steps by devices or components in embodiments are disclosed, including receiving a first set of electronic medical record data associated with a first patient during a first interval and calculating a first overall severity of illness score, as shown at 610. The first set of data can be one or more data points, such as a snapshot of vitals or other information relating to a patient received, for example, as captured at the beginning of a 24-hour period, and the first SOI score associated with this first set of EMR data can be calculated according to one more techniques described herein. At 614, a second set of electronic medical record data associated with the patient during a second interval is received and a second overall severity of illness score is calculated. In some cases, the data is associated with the patient during a second interval (for example from the beginning of a 24-hour period until hour eight, approximately, or as configured for capturing or factoring in certain data for a patient), but is not necessarily received by a system during that interval. For example, at the 24-hour mark or at some point after a threshold of data has been captured or accumulated, the sets or EMR data described herein can be received at the same or approximately the same time or in any order, as pushed or requested or available. As shown at 618, a third set of electronic medical record data associated with the first patient during a third interval is received and a third overall severity of illness score is calculated. At 622, a fourth electronic medical record data associated with the first patient during a fourth interval is received and a fourth overall severity of illness score is calculated.

Turning to 626, a first change in severity of illness score based on a difference between the second and first sets of EMR data (for example a difference between the second and first overall SOI scores) is calculated, and at 630 the first change is classified as Up, Flat, or Down, for example to the extent the second overall SOI score is greater or less than, or equal to, the first overall SOI score. At 634, a second change in SOI score based on a difference between the third and second sets of EMR data (for example the difference between the third and second overall SOI scores) is calculated, which is classified as Up, Flat, or Down at 638, for example to the extent the third overall SOI score is greater or less than, or equal to, the second overall SOI score. In some cases, "Up," "Down," and "Flat" as used herein means substantially or materially "Up," "Down," or "Flat," for example as set by parameters or thresholds or configured (e.g., where an institution or provider sets and/or refines the sensitivity or levels used), or as determined to be statically significant, recurring, or identified by models such as machine-learning approaches or regression analyses. At 642, a third change in SOI score based on a difference between the fourth and third sets of EMR data (for example the difference between the fourth and third overall SOI scores) is calculated, which is classified as Up, Flat, or Down at 646, for example to the extent the fourth overall SOI score is greater or less than, or equal to, the third overall SOI score.

In FIG. 6, at 650, a trend in the severity of overall illness score(s) associated with the first change, the second change, and/or the third change is detected, and, at 654, a risk of transfer for the first patient is determined based a trend in the severity of overall illness score data. As shown at 658, an output can be caused in some cases to be administered for the patient based on the risk, such as a warning on an interface or otherwise associated with a patient or patient's EMR that the patient has a risk of transfer, or an increase in treatment such as more frequent monitoring or data capture. An output may order one or more additional changes in severity of illness scores to be calculated, classified, and/or considered for the patient and, in some cases, it may update the risk of transfer after one or more additional intervals occur or are captured that provide set(s) of medical data.

Figure 7:
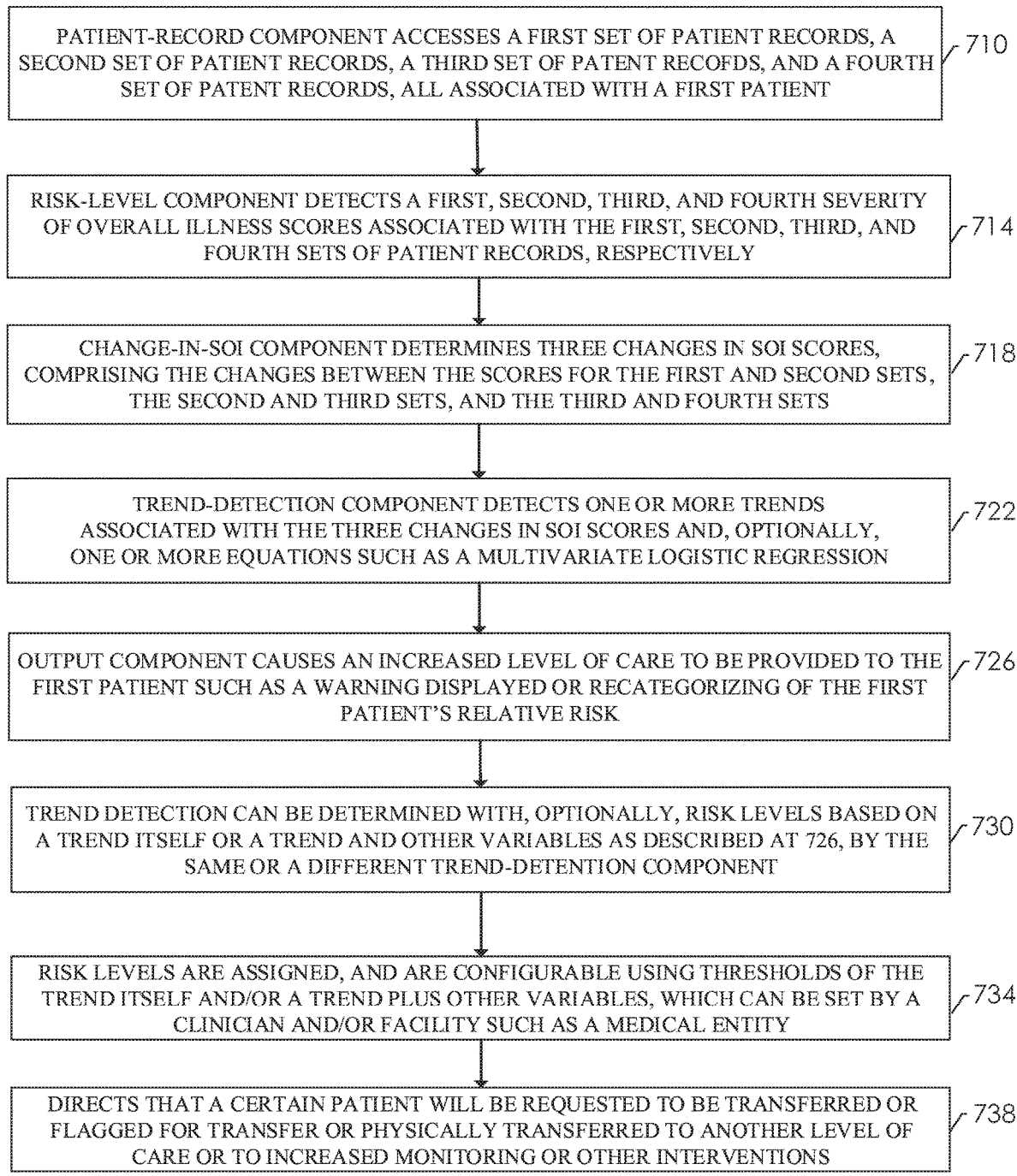
FIG. 7 is a diagram of aspects of systems in accordance with an embodiment of the present invention.

FIG. 7 likewise illustrates a diagram 700 of one or more potential processes included in some embodiments, such as a patient-record component accessing sets of patient data, such as electronic medical records, as shown at 710 (first, second, third, and fourth sets, in this example), and a risk-level component detecting four SOI scores associated with the sets (one each) at 714. At 718, a change-in-SOI component determines three changes in SOI scores, for example, and a trend-detection component at 722 detects one or more trends associated with these changes in SOI scores (and in some cases using one or more equations, as well). In embodiments, at 722, trend detection is determined and optionally risk levels are based on the trend itself and/or a trend plus other variables in an assignment of risk levels. A new or second trend can be an update based on three changes in SOI scores including a one or more new or additional changes in SOI scores, for example based on a fifth set of patient records (in some cases with one or more new or more-recent scores displacing an oldest or least-reliable SOI score in the analyses); and a trend in embodiments is continuously updated, such as with each new 8-hour interval that is captured or occurs, or being continually-refreshed with respect to three changes, for example, over the last four or most-recent SOI scores for a patient.

At 726, an optional output component causes an increased level of care such as a warning displayed using interface 400. At 730, trend detection can be determined with, optionally, risk levels based on a trend itself or a trend and other variables as described at 722, by the same or a different trend-detention component. At 734, risk levels are assigned, and are configurable using thresholds of the trend itself and/or a trend plus other variables, which can be set by a clinician and/or facility such as a medical entity. At 738, in an example, a system directs that a certain patient will be requested to be transferred or flagged for transfer or physically transferred to another level of care or to increased monitoring or other interventions. In embodiments, the same or a different trend-detection component detects a new trend associated with changes in SOI scores including a new or additional change in SOI score received by the system, for example after more time such as an 8-hour interval has passed, and a new trend is detected using, optionally, risk levels based on a trend itself or a trend and other variables.

In embodiments, the Delta or change in a Support Index over the prior 48 hours is the third largest driver in the model. In some cases, average Support Index scores decrease prior to discharge but increase prior to transfer. In some embodiments, four other independent variables can be considered as meeting the criteria for inclusion in the deterioration model (for example by meeting a P<0.001 criteria): female gender (related to an overall lower risk of deterioration), length of stay in the current level of care (log Daynum), length of stay in the hospital prior to the current level of care (preLOS), and having been transferred from an ICU to the current level of care. In embodiments, electronic health records are used to capture data at time intervals for these considerations. A high or critical risk of transfer flag is used in embodiments, based on a sequence of the last three changes in SOI scores in the 24-hour period leading up to a transfer for patients at risk, compared to patients that will be discharged normally.

In some cases, factors considered that can increase or decrease the risk of transfer for a patient can be ranked or considered in order of their effect on deterioration risk. For example, a patient's current SOI score can have the most effect in some cases and can be considered as increasing the risk of transfer of a patient to a different level of care or to more-frequent monitoring. The patient's need for support items in the last 24 hours or other time period can also be considered as having a relatively large effect on deterioration risk or on increasing the risk of transfer, in some cases. The factors discussed in this paragraph can be considered as discussed in descending order of effect on risk scores of a patient, in embodiments, if they exist. A range scaled support index value can also have a relatively large effect on the patient's risk scores, in some embodiments, also by increasing the risk of transfer, for example. The factors of a MAX measure of minRR, relating to blood pressure measurements, and a permanent pacemaker can both be considered as having an effect on risk scores including changes in scores over an interval, in some cases as decreasing the risk of transfer of the patient. In some cases, the factors of an antibiotic IV in the last 24 hours, a CAD or MI, or valve disease are considered as increasing the risk of transfer. In one example, the next factors in descending order of effect on risk scores are being female (gender) and a change in SOI score, with both of these factors potentially decreasing the risk of transfer of a patient. The factors of prior activity level of ICU, log Daynum, and bleeding can be considered as increasing the risk of transfer, as well as such factors as a high-risk transfer, previous length of stay, and cancer. These factors can be assigned coefficients reflecting their descending order of effect on deterioration risk, as reflected by the order discussed in this paragraph or as determined by calculations including using machine learning algorithms. The descending coefficients assigned to these factors (and others, in embodiments) can be used in equations to determine a patient's deterioration risk. In some cases, observations of data sets confirm the predictions based on these factors with only minor variations.

In embodiments of the present invention, patients are identified as being part of a "critical risk" category, for example based on their SOI score sequence over three intervals reflecting changes in SOI scores using data from four points (including no changes or no detectable or significant changes), and could be flagged based on various sensitivity levels. For example, if only one out of five identified patients are transferred, a sensitivity level is approximately 20% but specificity can be as high as 90%, for example. Adding additional monitoring sequences into the prediction of transfer can improve sensitivity, for example to a higher percent, such as over 45%, but may lower specificity and accuracy to less than 70%, for example.

In one example relating to GT 12-LE 24 hours, an equation for predicting deterioration can include a current SOI score, a range of scaled Support Index (for example the last 1 to 6 intervals), preLOS (e.g., LOS in prior location in fractional days), age, SDU, prior acuity level of ICU and/or ED, length of stay at current level of care, vital measures (e.g., maximum measure of minimum RR since admission and/or change in maximum heart rate), comorbidities (e.g., bleeding, cardiac arrest or myocardial infraction, and/or cancer), support (such as IV antibiotics since admission to the current location), and interactions (such as IV antibiotics relating to prior location acuity and/or cardiac arrest or myocardial infraction and prior location acuity). In another example relating to GT 24 hours, an equation for predicting deterioration can include a current SOI score, SOI sequence of three intervals, change in SOI score, range of scaled Support Index (for example the last 1 to 6 intervals), preLOS, gender such as female, SDU, prior acuity level, logDaynum of current level of care, vital measures (such as maximum measure of minimum RR since admission), comorbidities (bleeding, cardiac arrest or myocardial infraction, cancer, and/or valve disease), and/or support (IV antibiotics within 24 hours, permanent pacemaker, and/or total support items in the last 24 hours).

Users can view one or more deterioration risk categories, or patients included in or nor more categories for example by indicators, such as text including punctuation (e.g., an exclamation point or other symbol) and/or by color-coding or icons including graphic shapes, images, shading, or other visual representations of the risk categories associated with one or more patients. These risk categories can be based on one or more trends representing sequences of the last three changes in scores, for example severity of overall illness scores. As described herein, a certain trend can be detected based on changes of SOI scores over time intervals comprising Up, Up, Up, for example (or Up, Up, Flat; or in other cases Up, Flat, Up or Up, Flat, Flat) associated with data for the first patient, and in some cases this trend is the basis for a high or critical risk of deterioration or deterioration score that may result in more monitoring of the patient.

If a fifth data set is analyzed for a first patient to determine a fourth change in a score (for example at an 8-hour interval after the 24-hour mark, or sooner), then this fourth change (along with the second and third changes from a prior analysis—or the changes that rise above a threshold amount in some cases) can be used as the three changes in some cases, while excluding the fourth or oldest change available to determine a second trend. The first, second, third, and fourth sets of electronic medical record data associated with the first patient can be received without intervention by a medical professional or manual input in embodiments. A deterioration risk including its associated warning is displayed to users such as medical professionals in some cases, for example using an interface such as interface 400 discussed above, and an indication of risk can be color-coded and/or include text.

In some cases, a system for implementing patient care levels is used and includes a patient-record component that accesses first, second, third, and fourth sets of data or records associated with a first patient and a scoring component, wherein the scoring component determines a first score based the first set of patient data, a second score based on the second set of patient data, a third score based on the third set of patient data, and a fourth score based on the fourth set of patient data. Such a system may include a classifying component that classifies the first, second, and third changes, and a trend-detection component that detects a first trend associated with a first set of changes including the first, second, and third changes. Embodiments may also include a risk-level component that assigns a first level of risk for the first patient based on the first trend. One or more devices discussed in connection with the Figures herein including interface 400 can be used to display or access risk categories or warnings associated with embodiments.

For example, increases (such as above a threshold) comprising two or three of the three changes analyzed as a pattern or sequence by the system can cause a patient to be determined as having a "critical" risk of transfer, but embodiments can be created to allows a medical professional or entity to set one or more thresholds to fit their needs in terms of resources, acuity of patients, etc., and in some cases one or more threshold options are recommended to users, e.g., user 204, associated with a medical facility, for example, with options to view outcomes relating to setting each threshold at a higher or lower level. In embodiments, threshold values and other settings, including human interactions, can be analyzed from distributed sources such as various entities utilizing embodiments to enable embodiments of a system as described herein to provide up-to-date or more-comprehensive predictions or data points (including in some cases as determined from data with privacy restrictions where embodiments of a system as described herein can distill and/or provide certain information, such as recommendations without personally-identifiable information, without violating such restrictions).

In embodiments, systems and methods are provided that implement specific techniques relating to determining and/or addressing patients' needs or future odds of needing increased care. Systems can analyze electronic patient medical records accessed by the system from one or more distributed sources and identify trends associated with an increased rate of deterioration among a first subset of patients, compared to an earlier rate of deterioration, for example. In embodiments, identifying one or more trends (or individual changes in SOI scores between two data sets or time points) includes applying a first multivariate logistic regression.

In some examples, the amount or frequency of bedside interventions by nurses or other medical professionals is considered, in some cases as one factor, to determine whether a patient is deteriorating or deteriorating more quickly. Additionally, certain patients may have different criteria that affects the thresholds or levels or changes detected by embodiments of the present invention. For example, data relating to an elderly or ill patient, or a patient with clinical comorbidity, may be calibrated differently than data relating to a healthy patient. Subtle changes in EMR data for certain types of patients may cause a warning or alert even earlier for an ill or elderly patient, for example. In other cases, changes in EMR data for a healthy patient can trigger an alert sooner due to fewer expected changes.

Embodiments of the present invention can detect early, subtle signs of patients' needs for increased levels of care, in some cases before an event such a cardiac or respiratory event occurs. In some cases, more than one threshold is used, for example a first threshold for providing an alert that a patient needs an increased level of care (or for placing a warning, order, or command to transfer a patient), and a second-tier threshold for providing an alert or recommendation that a patient needs increased monitoring (or for causing an order or instruction to collect electronic medical data more frequently). For example, the first threshold could be if a patient is in the top 10% of patients most at risk of deterioration. In that case, a warning or command could be issued for patients in the top 10% relating to transfer of those patients. In embodiments, medical professionals or other decision-makers can configure the threshold values for transfer of a patient (or an alert relating to the likelihood of transfer) and for increased monitoring (or a warning or recommendation to increase monitoring, or in some cases the automatic increase of intervals for collecting medical data such as vital signs).

As described herein with reference to specific examples, embodiments of the present invention can monitor patients at greatest risk of deterioration, particularly patients outside of an ICU or critical care location. In embodiments, the calculations are based on data that is a by-product of clinical documentation and can provide alerts to clinicians at the patient's bedside in the best position to affect change for the patient. Embodiments of the present invention can expand the use of a Severity of Illness score to one that can be used within a deterioration model that automatically predicts and estimates risk of transfer for patients. Additionally, because the data and thresholds are based on EMRs including data collected or received in association with medical device(s), subtle changes that practitioners would not manually enter or recognize can be used (and at an earlier time than caregivers would implement), and continuous, accurate data and scoring can be implemented. In embodiments, the thresholds used are based on objective validations relating to transfer rates.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computer-implemented method of managing patient alerts, the method comprising:
   receiving a first set of electronic medical record data associated with a first patient during a first interval;
   calculating a first severity of illness score based on the first set of electronic medical record data;
   receiving a second set of electronic medical record data associated with the first patient during a second interval;
   calculating a second severity of illness score based on the second set of electronic medical record data;
   receiving a third set of electronic medical record data associated with the first patient during a third interval;
   calculating a third severity of illness score based on the third set of electronic medical record data;
   receiving a fourth set of electronic medical record data associated with the first patient during a fourth interval;
   calculating a fourth severity of illness score based on the fourth set of electronic medical record data;
   calculating a first change in severity of illness scores based on difference between the second severity of illness score and the first severity of illness score;
   calculating a second change in severity of illness scores based on a difference between the third severity of illness score and the second severity of illness score;
   calculating a third change in severity of illness scores based on a difference between the fourth severity of illness score and the third severity of illness score; and
   determining a first trend based on the first, second, and third changes in severity of illness scores.

2. The computer-implemented method of claim 1, further comprising determining a first deterioration risk associated with the first patient based on the first trend.

3. The computer-implemented method of claim 2, further comprising assigning a first classification to the first change, assigning a second classification to the second change, and assigning a third classification to the third change, wherein determining the first trend includes identifying the first, second, and third classifications as a first sequence of classifications.

4. The computer-implemented method of claim 3, wherein the first sequence of classifications includes at least two classifications that correspond to increases in severity of illness scores, and wherein the first trend is associated with a critical deterioration risk.

5. The computer-implemented method of claim 2, further comprising: receiving a fifth set of electronic medical data associated with the first patient; calculating a fourth change in severity of illness score; and determining a second trend based on the second, third, and fourth changes in severity of illness scores.

6. The computer-implemented method of claim 5, further comprising determining a second deterioration risk associated with the first patient based on the second trend; and directing an increase in monitoring of the first patient based on the second deterioration risk.

7. The computer-implemented method of claim 2, further comprising displaying a first indication of the first deterioration risk.

8. The computer-implemented method of claim 7, wherein the first indication is color-coded.

9. The computer-implemented method of claim 7, wherein the first indication includes text.

10. The computer-implemented method of claim 4, further comprising determining that the at least two classifications correspond to increases in severity of illness scores based on detected increases above one or more thresholds.

11. The computer-implemented method of claim 1, wherein the first, second, third, and fourth sets of electronic medical record data associated with the first patient are received without intervention by a medical professional.

12. A system for implementing patient care levels, the system comprising:
   a patient-record component, wherein the patient-record component accesses a first set of patient data associated with the first patient, a second set of patient data associated with the first patient, a third set of patient data associated with the first patient, and a fourth set of patient data associated with the first patient;
- a scoring component, wherein the scoring component determines a first score based on the first set of patient data, a second score based on the second set of patient data, a third score based on the third set of patient data, and a fourth score based on the fourth set of patient data; a classifying component, wherein the classifying component classifies a first change between the first and second scores, a second change between the second and third scores, and a third change between the third and fourth scores;
- a trend-detection component, wherein the trend-detection component detects a first trend associated with a first set of changes including the first change, the second change, and the third change; and
- a risk-level component, wherein the risk-level component assigns a first level of risk for the first patient based on the first trend.

13. The system of claim 12, wherein the first trend is associated with a first set of changes, the first change comprises a first increase between the first and second scores, and the second change comprises a second increase between the second and third scores.

14. The system of claim 12, wherein the first change is associated with a first rise in a score value, and second change is associated with a non-rise in the score value.

15. The system of claim 14, wherein the first level of risk indicates an above-average risk of transfer for the first patient.

16. The system of claim 12, wherein the first change is associated with a first rise in a score value, the second change is associated with a second rise in the score value, and the first level of risk triggers a warning.

17. A system for causing increases in patient care levels, the system comprising one or more computing devices executing computer-executable instructions to implement:
- analyzing electronic patient records including one or more electronic patient medical records accessed by the system from one or more distributed sources;
- identifying one or more patients associated with the electronic medical records;
- identifying one or more trends associated with an increased rate of deterioration among a first subset of the one or more patients associated with the electronic medical records, compared to an earlier rate of deterioration, wherein the one or more trends are determined based on one or more changes in rate between a first score and a second score based on electronic patient records; and
- increasing a first treatment level for the subset of the one or more patients based on the one or more trends.

18. The system of claim 17, further comprising providing for display the one or more patients based on a first deterioration risk category.

19. The system of claim 18, wherein the identifying one or more trends includes determining one or more first changes in rate between the first and second score, one or more second changes in rate between the second and third scores, and one or more third changes in rate between the third and fourth scores.

20. The system of claim 18, wherein identifying one or more trends includes applying a first multivariate logistic regression.

* * * * *